United States Patent [19]

Vasil et al.

[11] Patent Number: 5,405,765
[45] Date of Patent: Apr. 11, 1995

[54] METHOD FOR THE PRODUCTION OF TRANSGENIC WHEAT PLANTS

[75] Inventors: Indra K. Vasil; Vimla Vasil, both of Gainesville, Fla.

[73] Assignee: University of Florida, Gainesville, Fla.

[21] Appl. No.: 933,323

[22] Filed: Aug. 21, 1992

Related U.S. Application Data

[63] Continuation-in-part of Ser. No. 749,015, Aug. 23, 1991, abandoned.

[51] Int. Cl.6 ............ C12N 15/00; C12N 5/00; A01H 5/00; A01H 1/04
[52] U.S. Cl. .................. 435/172.3; 435/172.1; 435/240.1; 435/240.4; 435/240.49; 435/240.5; 800/200; 800/205; 800/250; 800/DIG. 58
[58] Field of Search ............ 435/170.1, 172.1, 172.3, 435/240.48, 240.1, 240.4, 240.49, 240.5; 800/205, 235, 200, 250, DIG. 58; 935/52

[56] References Cited

FOREIGN PATENT DOCUMENTS 3738874 11/1988 Germany.
9102071 2/1991 WIPO.

OTHER PUBLICATIONS

Chibbar et al. 1990. Journal of Cellular Biochemistry. 14E:277 (R111). Abstract.
Lonsdale et al. 1990. Journal of Experimental Botany. 41(230): 1161–1165.
Maddock et al. 1983. Journal of Experimental Botany. 34(144): 915–926.
Kartha et al. Mar. 1991. Symposium on Particle Bombardment–Mediated Transformation of Plant and Animal Systems. Madison, Wis. Abstract.
Redway et al. Aug., 1990, Plant Cell Reports. 3:714–717.
Hauptmann et al. 1988. Plant Physiology. 86:602–606.
Hess, Dieter, Klaus Dressler, and Rainer Nimmrichter (1990) "Transformation experiments by pipetting Agrobacterium into the spikelets of wheat (Triticum aestivum L.)" Plant Sci. 72(2):233–244–Biological Abstracts vol. 91, 1991, Philadelphia, Pa., US; abstract No. 57286.
Picard, E. (1988) "Blé transgénique: premier succés" Biofutur 72:12.
(1988) "Transformation du blé: Le tube de l'été" Biofutur 71:8–10.
Vasil, Vimla, Sherri M. Brown Diane Re, Michael E. Fromm, and Indra K. Vasil (1991) "Stably Transformed Callus Lines From Microprojectile Bombardment of Cell Suspension Cultures of Wheat" Bio/Technology 9(8):743–747.
Chen, D. F., N. P. Batty, J. Evans, and P. J. Dale (1990) "DNA delivery into regenerable tissues of wheat by microprojectile bombardment" Abstracts VIITH International Congress on Plant Tissue and Cell Culture-Meeting Held Jun. 24–29, 1990 p. 47 Abstract No. A2-12.
Vasil, Vimla, Ana M. Castillo, Michael E. Fromm, and Indra K. Vasil (1992) "Herbicide Resistant Fertile Transgenic Wheat Plants Obtained By Microprojectile Bombardment of Regenerable Embryogenic Callus" Bio/Technology 10(6):667–674.

(List continued on next page.)

Primary Examiner—David T. Fox
Assistant Examiner—Erich E. Veitenheimer
Attorney, Agent, or Firm—Saliwanchik & Saliwanchik

[57] ABSTRACT

The subject invention pertains to a novel method for producing transgenic wheat plants. The transgenic plants are produced by delivering appropriate DNA to a specific callus type.

2 Claims, 2 Drawing Sheets

OTHER PUBLICATIONS

Fromm, E. Michael, Fionnuala Morrish, Charles Armstrong, Rosalind Williams, John Thomas, and Theodore M. Klein (1990) "Inheritance and Expression of Chimeric Genes in the Progeny of Transgenic Maize Plants" Bio/Technology 8(9):833–839.

Redway, F. A., V. Vasil, D. Lu, and I. K. Vasil (1990) "Identification of callus types for long term maintainance and regeneration from commercial cultivars of wheat (Triticum aestivum L.)" Theor. Appl. Genet. 79(5):609–617–Biological Abstracts vol. 90, 1990, Philadelphia, Pa., US; abstract No. 46954.

Raineri, D. M., P. Bottino, M. P. Gordon and E. W. Nester (1990) "Agrovacterium–Mediated Transformation of Rice (Oryza Sativa L." Bio/Technology 8:33–38.

Gordon–Kamm et al. (1990) "Transformation of Maize Cells and Regeneration of Fertile Transgenic Plants" The Plant Cell 2:603–618.

Potrykus, Ingo (1990) "Gene Transfer to Cereals: An Assessment" Bio/Technology 535–542.

Potrykus, I. (1991) "Gene Transfer To Plants: Assessment of Published Approaches and Results" Annu. Rev. Plant Physiol. Plant Mol. Biol. 42:205–225.

Vasil, Indra K. (1990) "Transgenic Cereals Becoming a Reality" Bio/Technology 8:797.

Vasil, Indra K. (1988) "Progress in the Regeneration and Genetic Manipulation of Cereal Crops" Bio/Technology 6:397–402.

METHOD FOR THE PRODUCTION OF TRANSGENIC WHEAT PLANTS

CROSS-REFERENCE TO RELATED APPLICATION

This is a continuation-in-part of application Ser. No. 07/749,015, filed Aug. 23, 1991, now abandoned.

BACKGROUND OF THE INVENTION

More than 50% of the food used by man is provided by a single group of crop plants, the cereals, of which wheat is the most important species. Biotechnological methods, which provide new and unique opportunities for the genetic improvement of this crop, require efficient plant regeneration in vitro and the recovery of transgenic plants following delivery and integration of foreign genes into regenerable cells (Vasil, I. K. [1988] Bio/Technology 6:397–401).

A transgenic plant can only result from integrative transformation of a totipotent cell or a cell that has a clonal connection to the "germline." A number of methods have been proposed and used for the genetic transformation of plants, including cereal species (Vasil, I. K. [1990] Bio/Technology 8:797; Potrykus, I. [1991] Ann. Rev. Plant Physiol. Plant Molec. Biol. 42:205–225; Vasil, V., A. M. Castillo, M. E. Fromm, I. K. Vasil [1992] Bio/Technology 10:667–674). Examples of some of these methods, as outlined below, illustrate the breadth of techniques which have been attempted for producing transgenic cereals but have been unsuccessfully applied to wheat.

Agrobacterium and Cereals

The tumor-inducing (Ti) plasmid of *Agrobacterium tumefaciens* has been shown to introduce foreign genetic information into plant cells. International Publication No. WO84/02920. However, *A. tumefaciens* is incapable of infecting monocotyledons, such as cereals. Therefore, it does not transfer DNA to these types of plants, such as wheat. The recent report of transgenic wheat obtained by using Ti from Agrobacterium (Hess, D., K. Dressier, R. Nimmrichter [1990] Plant Sci. 72:233–244), can be considered artifactual based on criteria used to demonstrate transformation (Potrykus, I. [1991], supra; Potrykus, I. [1990] Bio/Technology 8:535–542). Raineri et al. (Raineri, D. M., P. Bottino, M. -P. Gordon, E. W. Nester [1990] Bio/Tech. 8:33–38) presented evidence giving a reasonable inference of Agrobacterium-mediated transformation of rice cells (*Oryza sativa*), although definitive proof is still lacking.

Agroinfection and Cereals

Agroinfection has been shown to lead to systemic spread of maize streak virus. This showed for the first time that Agrobacterium can transfer its T-DNA to cereal cells. Later it was demonstrated that the efficiency of transfer is comparable to dicot systems. In cereals, agroinfection leads to the transfer of the virus-carrying T-DNA into wound-adjacent cells. The virus is released, replicates, and spreads systemically. Even if it reaches rare competent cells somewhere in the plant body it does not integrate. Thus the chances that agroinfection will produce transgenic cereals are minimal and no different from normal Agrobacterium infection.

Viral Vectors

Viruses spread systemically throughout the plant from the infection site and can replicate many thousands of copies per cell. According to the available evidence, viruses do not integrate into the host genome and they are excluded from meristems and thus from transmission to sexual offspring.

Incubation in DNA of Dry Seeds or Embryos

Thus far, no transgenic plants have been recovered using this method. Incubation of seeds in DNA has yielded indicative evidence since the 1960s. However, no proof for transformation has ever been presented. Although some experiments clearly demonstrate the presence and expression of defined marker genes as well as the replication of engineered viral DNA, they do not provide proof for transformation. The conclusion that the data demonstrate uptake of the foreign DNA into the cells of the embryos is merely one hypothesis. It is not possible to exclude the alternative hypothesis that the DNA data are the result of open cells at the large wound site and that the virus DNA data are, in addition, due to systemic spread.

Incubation in DNA of Tissues or Cells

No transgenic tissues or plants have been recovered. There have been many approaches where seedlings, organs, tissues, cells, or cell cultures of numerous plant species have been brought into direct contact with foreign DNA and defined marker genes. Even in experiments that would have recovered extremely rare events of integrative transformation, there is not a single proven case of integrative transformation.

Pollentube Pathway

No transgenic plants have been recovered from this method. Integration into high molecular weight DNA and defined hybrid fragments has not been shown.

Liposome Fusion with Tissues and Protoplasts

Fusion of DNA-containing liposomes with protoplasts is an established method for the production of transgenic plants. DNA-containing liposomes have also been applied to various tissues, cell cultures and pollen tubes, with the rationale that liposomes might help transport the DNA via plasmodesmata or directly across the cell wall. It has been shown that liposomes can carry small dye molecules into cells within tissues via fusion with the plasmalemma. There is, however, no proof for transport and integration of marker genes. As plasmodesmata are sealed off immediately upon wounding, this route is not open even for small liposomes. Integration of the cell wall with phospholipids does not seem to change its barrier function. No transgenic cereals have been obtained by this method.

Liposome Injection

Thus far no transgenic tissue has been recovered by this method. Microinjection of DNA has yielded transgenic chimeras. Microinjection into differentiated cells can easily deposit the DNA into the vacuole, where it is degraded. Microinjection of liposomes into the vacuole leads to fusion with the tonoplast thus releasing the content of the liposome into the cytoplasm, as demonstrated with cytoplasm-activated fluorescent dyes.

Protoplasts and Direct Gene Transfer

Protoplasts efficiently take up DNA if treated with polyethylene glycol (PEG) and/or electroporation. When protoplasts are transformed that are also competent for regeneration, transgenic plants can be recovered that stably contain, express, and inherit the foreign gene. Protoplasts isolated from intact cereal plants do not contain cells competent for regeneration. Competent protoplasts have, so far, been isolated only from embryogenic suspensions established from immature tissues (scutellum, leaf base, anther). Standard direct gene transfer procedures with protoplasts from embryogenic suspensions has led to the regeneration of transgenic rice (*Oryza sativa* var. japonica and indica) and maize (*Zea mays*). However, the establishment of the appropriate cell cultures is an art that depends upon parameters which are difficult to control.

Protoplasts from Cereal Plants

No transgenic clones have been recovered by this method. As the establishment of appropriate embryogenic suspensions is a delicate and often unpredictable process, it would be of great advantage if protoplasts isolated directly from differentiated tissues could be cultured. However, this approach appears, to date, rather hopeless because differentiated cereal tissues do not express the wound response and do not contain cells competent for regeneration. DNA uptake is no problem, as can be shown easily with transient expression assays. If integration occurs it has no consequences, because protoplasts do not proliferate.

Biolistics or Particle Gun

Acceleration of heavy particles covered with DNA has been used with some success to transport genes into plant cells and tissues. Transgenic plants have been produced in soybean and tobacco. The method has the potential for general applicability: (1) it is easy to handle; (2) one shot can lead to multiple hits; (3) cells survive the intrusion of particles; (4) the genes coated onto the particle resume biological activity; (5) target cells can be as different as pollen, cell cultures, plant organs, and meristems; (6) particles also reach deeper cell layers. Thus, the method provides a biological vector-independent DNA delivery system. Transgenic maize plants have been obtained by the delivery of DNA-coated particles into plated suspension cultures (Fromm, M. E., F. Morrish, C. Armstrong, R. Williams, J. Thomas, T. M. Klein [1990] *Bio/Technology* 8:833-839; Gordon-Kamm, W. J., T. M. Spencer, M. L. Mangano, T. R. Adams, R. J. Daines, W. G. Start, J. V. O'Brien, S. A. Chambers, W. R. Adams Jr., N. G. Willetts, T. B. Rice, C. J. Mackey, R. W. Krueger, A. P. Kausch, and P. G. Lemaux [1990] *The Plant Cell* 2:603-618). Bombardment of intact embryos, pollen and other tissues has not yielded any transgenic wheat.

Microinjection

No transgenic offspring have been recovered so far in cereals using this method. Microinjection uses microcapillaries and microscopic devices to deliver DNA into defined cells in such a way that the injected cell survives and can proliferate. This technique has produced transgenic clones from protoplasts (where transformation via direct gene transfer is easier) and transgenic chimeras from microspore-derived proembryos in oilseed rape. As with biolistics, microinjection definitely delivers DNA into cells. Extensive experiments with many species, including cereals, have not definitively produced any transgenic plants.

Pollen Transformation

No transgenic plants have been produced by this method. This approach is based on the hope that DNA could be taken up into germinating pollen and either integrate into the sperm nucleus or reach the zygote with the pollen tube. Numerous large-scale experiments in experienced laboratories with defined marker genes have only given clearly negative results. Therefore, it is justified to conclude that this approach is not a very promising one.

Electroporation

No transgenic clones have been produced when applied to cells and tissues. Not much potential is expected with walled cells. This is a routine method for gene transfer to protoplasts but transfer of genes into walled cells has not been possible.

In summary, the two methods found useful for delivery of DNA into cells of cereal plants which result in stable transformation are electroporation or polyethylene glycol treatment into protoplasts, and more recently, accelerated particle bombardment into plated suspension cultures or calli. Attempts at producing transgenic wheat plants, however, proved unsuccessful, although methods were utilized that were previously successfully applied to the regeneration of other plants, including other cereals.

Following is a summary of the methods attempted to obtain stably transformed callus tissues and plants of wheat. These methods, though previously shown to transform cereal plants such as rice and maize, failed to result in the production of viable wheat plants.

1. Protoplasts

Plasmid DNA containing NPTII and GUS genes was introduced into embryogenic protoplasts by the PEG method. A number of cell colonies selected on kanamycin media tested positive for GUS activity. Plants were obtained from these colonies. However, Southern analyses provided no evidence for the presence of either the NPTII or the GUS gene. It was therefore concluded that the available protoplast system was not suitable for obtaining transgenic plants of wheat.

2. Suspension Culture

Next, plasmid DNA containing NPTII, GUS, and EPSPS genes was delivered into intact plated suspension culture cells by bombardment with accelerated microprojectiles (Vasil, V., S. M. Brown, D. Re, M. E. Fromm, I.K. Vasil [1991] *Bio/Technology* 9:743-747). Calli resistant to kanamycin and showing GUS expression were shown by Southern analyses to have integrated each of the three genes. Expression of the genes was demonstrated by NPTII and EPSPS activity. No transgenic plants were recovered from the transformed calli.

3. Immature Embryos

Next, immature zygotic embryos of wheat were bombarded with DNA-coated macroprojectiles at various intervals after excision and culture. Transient expression of the GUS gene was demonstrated, but no stably transformed callus lines or plants were obtained.

Thus, the methods known in the art to show the greatest potential for producing transgenic plants did not viably transform wheat plants, even though success had been shown in rice and maize.

BRIEF SUMMARY OF THE INVENTION

The subject invention concerns a method for producing transgenic wheat plants. In accordance with this invention, wheat plants can be grown which express one or more of a variety of genes. These genes may, for example, confer upon said transformed plant resistance to herbicides or disease, or they may function to alter the nutritional value of the wheat. There are many genes which are known and readily available to those skilled in this art which could be used in conjunction with the methods of the subject invention.

The method described in detail herein pertains to the transformation of Type C embryogenic calli of wheat with appropriate genetic material. Type C calli are reliably produced according to the procedures described herein. These calli can then be transformed with the appropriate genetic material to surprisingly, and advantageously, produce transformed calli which then can be grown into healthy plants.

In a preferred embodiment of the subject invention, the Type C embryogenic calli are transformed by bombardment with DNA-coated microprojectiles. Advantageously, the transformed plants resulting from the subject method are themselves capable of producing transgenic progeny.

Further aspects of the subject invention include the transformed wheat plants produced according to the procedures described herein, as well as transgenic seed and transgenic progeny resulting therefrom.

DETAILED DESCRIPTION OF THE INVENTION

Figure 1:
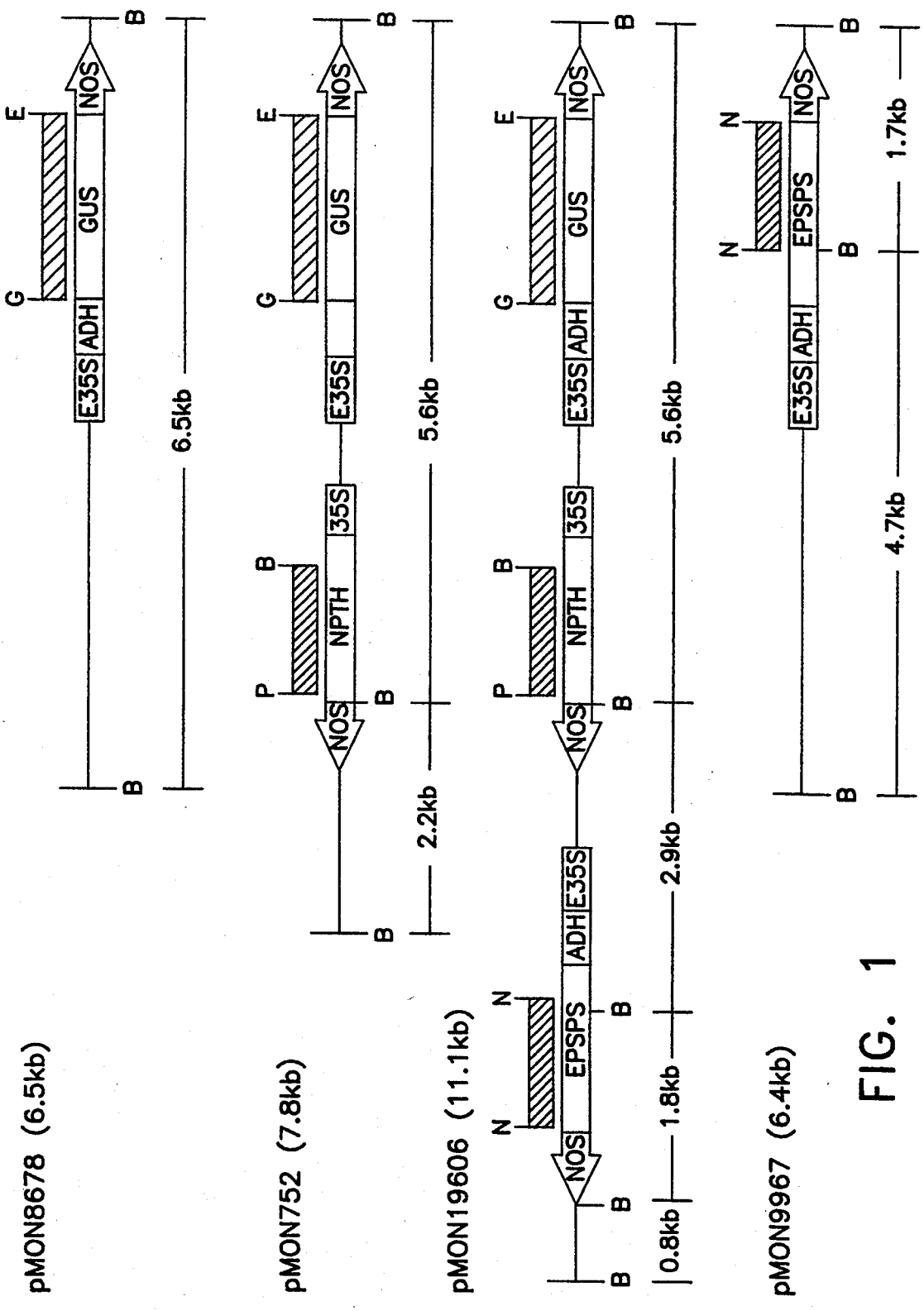
FIG. 1. Maps of plasmids used in transformations. The white boxes indicate regions responsible for plant gene expression. Horizontal lines indicate pUC plasmid sequences. Striped boxes show fragments used to probe Southern blots. Relevant restriction sites are indicated: B=BamHi, E=EcoRI, G=BglII, N=NcoI, P=PstI. Legends for white boxes: E35S=enhanced 35S promoter of CaMV, ADH=first intron from the maize alcohol dehydrogenase gene, GUS=β-glucuronidase gene from *E. coli*, NOS=nopaline synthase gene, NTPII=neomycin phosphotransferase gene, EPSPS=5-enopyruvylshikimate phosphate synthase gene.

The subject invention provides, for the first time, a method for the production of transgenic wheat plants. As described in the Background of the Invention, previous efforts to produce transgenic wheat plants have been unsuccessful despite considerable efforts and success in other cereals. We have discovered that transformation of a particular type of wheat callus results in a stable and permanent integration of the DNA of interest, such that plants can be grown and the transformation passed on to subsequent generations.

One preferred embodiment of the subject invention pertains to the production of transgenic wheat plants by a process comprising bombarding a novel Type C embryogenic wheat callus with plasmid DNA comprising desired genes to obtain transgenic wheat plants.

The method of the subject invention can be thought of as a two-step process. The first step involves obtaining Type C embryogenic wheat calli. The second step involves transforming the calli obtained in the first step with appropriate DNA. Each of the two steps are described in detail herein.

In one embodiment of the subject invention, *Escherichia coli* β-glucuronidase (GUS) and *Streptomyces hygroscopicus* bar genes can be transformed into the wheat plants. The bar gene confers herbicide (Basta ®; Hoescht AG, Frankfurt, Germany) resistance to the plants by encoding phosphinothricin acetyl transferase (PAT), which inactivates phosphinothricin (PPT), the active ingredient of Basta ®. In this embodiment, selection can be made on Basta ®, and the surviving calli further screened for GUS expression. From four experiments, using two cultivars of wheat (Pavon and RH770019), we have selected four independent transformed calli. Transgenic flowering plants have been recovered. Transgenic seed was produced, which yielded transgenic progeny. Presence of a functional bar gene in the plants has been confirmed by Southern analysis and PAT activity assays. Thus, transgenic wheat plants can be obtained by the direct delivery of DNA into Type C regenerable embryogenic calli. Such calli can be obtained in accordance with the teachings of the subject invention in various cultivars of wheat.

The Type C callus obtained and used according to the subject invention is obtained by tissue culture techniques which are described in detail below. The exact procedures used to obtain the Type C calli may be varied somewhat by persons skilled in the art. The critical aspect of this step of the inventive method is that a callus is obtained which can be transformed with appropriate DNA and, most importantly, the transformed callus can be grown to maturity and express the exogenous gene(s).

We have found that immature embryos, inflorescences, and anthers of eight commercial cultivars of *Triticum aestivum* (wheat) formed embryogenic callus on a variety of media. Immature embryos (1.0-1.5 mm long) were found to be most suitable for embryogenic callus formation while anthers responded poorly; inflorescences gave intermediate values. Immature embryos of various cultivars showed significant differences in callus formation in response to 11 of the 12 media tested. No significant differences were observed when the embryos were cultured under similar conditions on MS medium with twice the concentration of inorganic salts, supplemented with 2,4-D, casein hydrolysate and glutamine. Furthermore, with inflorescences also, no significant differences were observed.

Explants on callus formation media formed two types of embryogenic calli: an off-white, compact and nodular callus, and a white compact callus. Upon successive subcultures (approximately 5 months), the nodular embryogenic callus became more prominent and was identified as "aged callus." This "aged callus" is the type of callus we have termed "Type C" and is the callus which is used for transformation with appropriate DNA according to the subject invention. The aged callus can be obtained approximately 1-8 months after culture initiation.

The aged callus, upon further subculture, formed an off-white, soft, and friable embryogenic callus. Both the aged and friable calli maintained their embryogenic capacity over many subculture passages (to date up to 19 months). All embryogenic calli (1 month old) from the different callus-forming media, irrespective of explant source, formed only green shoots on regeneration media that developed to maturity in the greenhouse. There were no significant differences in the response of calli derived from embryos and inflorescences cultured on the different initiation media. Also, the shoot-forming capacity of the cultivars was not significantly different. Anther-derived calli formed the fewest shoots. Aged and friable cells on regeneration media also formed green shoots but at lower frequencies. Plants from long-term culture have also been grown to maturity in soft.

The Type C calli obtained as described herein are transformed with DNA comprising desired genes. For example, genes which confer upon the transformed wheat resistance to herbicides is particularly advantageous. The bar gene is an example of a gene which confers herbicide resistance upon the transformed plant. Fields of herbicide-resistant wheat can then be treated with herbicide to control weeds without adversely affecting the desired wheat crop. The wheat may also be transformed with genes which confer resistance to pathogens, diseases, or pests. For example, a number of *Bacillus thuringiensis* genes which express proteins toxic to nematode, coleopteran, and lepidopteran pests are well known and readily available to those skilled in this art. Furthermore, the plants may be transformed with genes which, when expressed, will alter the nutritional makeup of the wheat.

The calli may be transformed using any method which stabilizes integration of the desired DNA within the plant cell. We have found bombardment with DNA-coated microprojectiles to be particularly well suited for wheat transformation. Other methods may also be used by those skilled in this art.

Materials and Methods

Plant Material

Immature embryos, inflorescences, and anthers of eight commercial cultivars of wheat (*Triticum aestivum* L.) were used as explants for callus formation and later plant regeneration. These cultivars were 'Anza,' 'Chris,' 'Coker983,' 'FLA301,' 'FLA302,' 'Fremont,' 'Hunter,' and 'Pavon.' Explants were taken from plants grown in the field as well as in the green house (immature embryos only). Field plantings were made between October and December. For greenhouse-grown material, seeds were planted between January and March in pots containing Terra-Lite metro-mix growing medium. The growing season lasted approximately 3 months.

Immature caryopses (10–12 days post-anthesis), and inflorescences (5–20 mm long, from young shoots prior to the emergence of the flag leaf) were surface-sterilized with 70% ethanol (30 seconds) and 20% NaOCl (10–15 minutes), followed by four changes of sterile distilled water. Immature embryos, 0.5–1.5 mm long, were dissected under a stereo dissecting microscope, and the inflorescences were cut into approximately 1 mm long segments prior to culture. Spikes were pretreated at 4° C. in total darkness for 4–7 days before anther culture. Spikes were surface-sterilized with 70% ethanol (60 seconds), 10% NaOCl (10 minutes) and washed with four changes of sterile water. Anthers containing microspores at the uni-nucleate stage were aseptically removed and placed in culture.

Initially immature embryos were cultured on MS (Murashige, T., F. Skoog [1962] *Physiol. Plant* 15:473–497), MSAA (Muller, A. J., R. Grafe [1978] *Mol. Gen. Genet.* 161:67–76), and C$_8$ (Dudits, D., G. Hadlaczky, E. Levi, O. Fejer, Z. Haydu, G. Lazar [1977] *Theor. Appl. Genet.* 51:127–132) media with 3% sucrose and 2 mg l$^{-1}$ 2,4-dichlorophenoxyacetic acid (2,4-D). Later, callus was initiated from inflorescences and immature embryos on MS medium with 2,4-D, dicamba, twice the concentration of MS inorganic salts (Ozias-Akins, P., I. K. Vasil [1983] *Protoplasma* 117:40–44), potato extract (Chuang, C. C., J. W. Ouyang, H. Chia, S. M. Chou, C. K. Ching [1978] In *Proc. Symp. Plant Tiss. Cult.*, Science Press, Peking, pp. 52–56), casein hydrolysate, glutamine, silver nitrate, and cefotaxime. Cefotaxime was filter-sterilized and added to the autoclaved media (15 psi, 121° C., 18 minutes) while all other additives were added to the media before autoclaving. Gelrite was added at 0.2%.

Anthers were cultured on solid and/or liquid N$_6$ (Chu, C. C., C. C. Wang, C. S. Sun [1975] *Sci. Sin.* 118:659–668), P$_2$ (Chuang et al. [1978], supra), and WM2 (Datta, S. K., G. Wenzel [1987] *Plant Sci.* 48:49–54) media. Liquid cultures consisted of anthers dispersed in 2 ml medium in 5.5 cm petri dishes. The cultures were replenished with 1 ml fresh medium at 2-week intervals. Other media were solidified with 0.6% agar.

Large numbers of immature embryos, inflorescences, and anthers were cultured on each medium. Immature embryos were cultured with the scutellum away from the surface of the growth medium. Embryo and inflorescence cultures were incubated at 28° C. in total darkness for 4 weeks. Anthers were incubated at 30° C. and total darkness for 6–8 weeks.

At the end of each growth period, embryogenic callus formation was assessed in all the explant types. Embryogenic calli were then transferred to regeneration as well as maintenance (inflorescences and embryos only) media. For regeneration, immature-embryo-derived embryogenic calli (1 month old) were transferred from the 12-callus formation media to MS medium with 1 mg l$^{-1}$ indole-3-acetic acid (IAA) and 1 mg l$^{-1}$ zeatin (Ozias-Akins, P., I. K. Vasil [1982] *Protoplasma* 110:95–105).

Later, aged and friable calli were placed on the same medium as well. Inflorescence-derived embryogenic calli (1 month old) were transferred to MS medium with 0.2 mg l$^{-1}$ 2,4-D and 1 mg l$^{-1}$ 6,γγ-dimethylallylaminopurine (2iP) (Ozias-Akins and Vasil [1982], supra) and calli derived from anthers on P$_2$ solid medium with 0.5 mg l$^{-1}$ naphthaleneacetic acid (NAA) and 0.5 mg l$^{-1}$ kinetin (Ouyang, J. W., S. M. Zhou, S. E. Jia [1983] *Theor. Appl. Genet.* 66:101–109). For each treatment, between 10 and 30 callus pieces were transferred to the regeneration media and maintained at 28° C. with a 16-hour photoperiod. Shoot formation was assessed after 4 weeks.

For the maintenance of embryogenic callus, the more compact organized pieces, and later the friable calli as well, were transferred to maintenance medium and subcultured at 4-week intervals. Cultures were incubated at 28° C. in total darkness.

Regenerated plantlets, 10–15 mm high, were hardened by transfer to Magenta vessels containing MS medium without growth hormones and later to Conetainers with Terra-Lite metro-mix growing medium. After 2 weeks on a light cart, plants were transferred to the greenhouse. Plantlets derived from aged calli were also hardened by transfer to MS hormone-free medium or rooting media; MS (half strength) only, or MS (half strength) with varying concentrations of NAA, IAA, and indolebutyric acid (IBA). Plantlets were transferred directly from the regeneration of rooting media to pots of Vermiculite A3 for further rooting. Plantlets were maintained at 28° C. with a 16-hour photoperiod and high humidity.

Some of the abbreviations used herein are as follows: MS1=MS+1 mg l$^{-1}$ 2,4-D; MS2=MS+2 mg l$^{-1}$ 2,4-D; MS2P=MS+2 mg l$^{-1}$ 2,4-D+5% potato extract; MS(x2),2=MS(twice concentration)+2 mg l$^{-1}$ 2,4-D; MS2CH,G=MS+2 mg l$^{-1}$ 2,4-D+100 mg l$^{-1}$ casein hydrolysate+500 mg l$^{-1}$ glutamine; MS(x2),2CH,G=MS(twice concentration)+2 mg l$^{-1}$ 2,4-D+100 mg l$^{-1}$ casein hydrolysate+500 mg l$^{-1}$ glutamine; MS2Ag5=MS+2 mg l$^{-1}$ 2,4-D+5 mg l$^{-1}$ silver nitrate; MS2Ag10=MS+2 mg l$^{-1}$ 2,4-D+10 mg l$^{-1}$ silver nitrate; MS2Cf50=MS+2 mg l$^{-1}$ 2,4-D+50 mg l$^{-1}$ cefotaxime; MS2Cf100=MS+2 mg l$^{-1}$ 2,4-

D+100 mg l$^{-1}$ cefotaxime; MS1D=MS+1 mg l$^{-1}$ dicamba; MS2D=MS+2 mg l$^{-1}$ dicamba.

Immature embryos of wheat (*Triticum aestivum* L. cv Pavon and RH770019) were used to initiate embryogenic callus (Redway, F. A., V. Vasil, D. Lu, I. K. Vasil [1990] *Theoret. Appl. Genet.* 79:609–617). The callus was subcultured once a month. After 4–5 months, localized areas of the more compact and organized Type C callus were identified (Redway, F. A., V. Vasil, I. K. Vasil [1990] *Plant Cell Rep.* 8:714–717). Portions (1–3 mm) of 5–7 month old Type C callus were separated and transferred to the center of a petri dish (LabTek 60×20 mm) containing MS1 medium (Murashige and Skoog, supra salts and vitamins, 100 mg/l inositol, 2% sucrose, 1 mg/l 2,4-D), and solidified with 0.2% gelrite. 20–25 pieces were placed in each dish.

The data were analyzed assuming binomial sampling models using arc sin transformations on the proportion of callus and shoot formation. The weighted least-squares and the Type III sum of squares of analyses were used to draw conclusions on the basis of F-tests ($\alpha=0.05$). The more interesting interactions were further analyzed by pair-wise multiple comparison tests at a 5% level of significance.

Microprojectile Bombardment

Plasmid DNA (5 μg/ml) was adsorbed to the surface of tungsten particles (0.73 μm; 25 μl) with 1M CaCl$_2$ (25 μl) and 0.1M spermidine free base (10 μl) in a 0.5 ml Eppendorf tube. Gold particles can also be used. After 10 minutes incubation, 45–50 μl of the supernatant was discarded from each tube. The DNA-tungsten mixture (2.5 μl) was loaded on a macroprojectile after brief sonication. Plated calli were bombarded under partial vacuum (28 mm Hg) at a distance of 13 cm from the stopping plate, with the Dupont PDS-1000 apparatus.

Histochemical Staining for GUS Expression

Transient expression of the GUS gene was visualized by transferring the filter containing either 2 or 14 day old bombarded cells to filter-sterilized GUS substrate mixture and incubating overnight at 37° C. The number of cells or cell aggregates developing a blue color/precipitate, indicating GUS positive expression, were counted under a dissecting microscope. Calli bombarded without DNA served as controls.

Basta ® Selection

The bombarded calli were left in the same nutrient medium for 1–2 weeks, and then placed in larger dishes (100×20 mm) containing MS1 medium supplemented with 1 mg/l Basta ® (MS1B1), the ammonium salt of phosphinothricin (20% active ingredient). The calli were then transferred every 2 weeks to successively higher levels of Basta ® (5, 10, 20, and 40 mg/l). Calli surviving on MS1B40 were maintained by subculture to fresh medium every 3 weeks.

Plasmids

The following five plasmids were used either separately or in combination: pMON8678 containing the GUS gene, pMON752 containing the GUS and the NPTII genes, pMON9967 with the EPSP synthase gene, and pMON19606 with the GUS, NPTII and EPSP synthase genes. Details of the plasmids are shown in FIG. 1. These plasmids were constructed by inserting the 0.6 kb cauliflower mosaic virus (CaMV) 35S RNA promoter (E35S) containing a duplication of the −90 to −300 region, a 0.58 kb fragment containing the first intron from the maize alcohol dehydrogenase gene, and the 3' termination sequences from the nopaline synthase (NOS) gene into pUC19. The coding sequences from the *E. coli* GUS gene or a glyphosate-tolerant variant of the maize EPSP synthase (Gasser et al. in preparation) were inserted to form pMON8678 or pMON9967, respectively. pMON752 is identical to pMON8678, except that a fragment for kanamycin selection of transformed plant cells has been included. This fragment contains the NPTII coding sequence driven by a 0.35 kb CaMV 35S promoter (without the upstream duplication) and terminated by NOS sequences. pMON19606 was constructed from pMON752, with the E35-S/ADH/EPSPS/NOS fragment from pMON9967 inserted within the pUC sequences.

Plasmid

The plasmid pBARGUS (FIG. 2) is described elsewhere (Fromm et al. [1990] *Bio/Technology*, supra). The Adh1 promoter, attached to the Adh1 intron 1 fragment, is used to drive the expression of the GUS reporter gene (Jefferson, R. A. [1987] *Plant Mol. Biol. Rep.* 5:387–405). The CaMV 35S promoter, attached to the Adh 1 intron 1, drives the selectable bar gene that confers resistance to the herbicide Basta ®.

Assay for PAT Activity

Crude extracts of protein were prepared in 50 mM Tris HCl, pH 7.5, 2 mM EDTA, 0.15 mg/l leupeptin, 0.15 ml/l phenylmethylsulfonyl fluoride (PMSF), 0.3 mg/l BSA, 0.3 mg/l DTT. After clarification, protein concentration was determined by the BioRad microprotein assay with BSA as a standard. PAT activity was determined using 50 μg protein from each sample as per Spencer et al. (Spencer, T. M., W. J. Gordon-Kamm, R. J. Daines, W. G. Start, P. G. Lemaux [1990] *Theoret. Appl. Genet.* 79:625–631).

Plant Regeneration

Portions of callus from all Basta ®-resistant lines showing PAT activity were placed on regeneration medium (MS with 1 mg/l each of zeatin and indole-3-acetic acid) in light, as described previously (Redway et al. [1990] *Theoret. Appl. Genet.*, supra). Following testing for the effect of three concentrations (5, 10, and 20 mg/l) on regeneration, 20 mg/l Basta ® was included in all regeneration media until the regenerated plants were at least one inch tall. Rooted plants were transferred to soil in Conetainers and finally to soil in pots (Redway et al., supra). Plants were grown to maturity in a growth room.

DNA Isolation and Southern Hybridization

Genomic DNA was isolated from the four PAT positive callus lines, leaves of ten R0 plants that tested positive for PAT activity, leaves of R1 plants, and the controls. The tissues were ground to a fine powder in liquid nitrogen and DNA was isolated according to the CTAB protocol (Lassner, N. W., P. Peterson, J. I. Yoder [1989] *Plant Mol. Biol. Rep.* 7:116–128). Plant as well as plasmid DNA was digested with BamHI, electrophoresed through 0.8% or 1.2% agarose and transferred (Southern, E. M. [1975] *J. Mol. Biol.* 98:503–517) to nylon membranes (Hybond N, Amersham). The 0.5 kb bar fragment was released from the pBARGUS plasmid by Kpn1/BamHI digestion, and the 1.8 kb GUS fragment was released from the same plasmid by PstI digestion. Radioactive probes were made with $^{32}$P using random-primed labeling (Feinberg, A. P., B. Vogelstein [1983] *Anal. Biochem.* 132:6–13). The prehybridized blots were hybridized with the bar or GUS probes overnight at 65° C., and washed three times with sodium phosphate buffer (pH 7.2) and 1% SDS at 65° C. for 5, 30, and 15 minutes and visualized by autoradiography.

Following are examples which illustrate procedures, including the best mode, for practicing the invention. These examples should not be construed as limiting. All percentages are by weight and all solvent mixture proportions are by volume unless otherwise noted.

EXAMPLE 1

Basal Media

Immature embryos formed embryogenic callus on all three basal media tested. However, callus formation on MS medium was significantly higher than on MSAA or $C_8$. Some cultivars formed no callus on $C_8$ medium. MSAA medium differs from MS medium in the replacement of ammonium and potassium nitrate with potassium chloride and an amino-acid mixture of glutamine, glycine, arginine, and aspartic acid. The replacement of MS nitrates with the amino-acid mixture was of no benefit to callus formation from immature embryos. The components of $C_8$ medium are different from those of MS or MSAA. In addition to the macro- and microelements, $C_8$ medium contains organic complexes such as urea, ammonium citrate, and yeast extract. Even though $C_8$ medium is specifically suited for the maintenance of cell suspensions initiated from mature-seed-derived callus of *Triticum monococcum* (Dudits et al. [1977], supra), it supported very little growth of immature embryos of *T. aestivum*.

EXAMPLE 2

Media Supplements for Optimum Response

Immature embryos of all cultivars formed embryogenic callus on the 12 media tested. The percentage callus formation ranged from 6.7% to 100%. In many of the treatments, embryogenic callus formation was 50.0% or greater. There were significant differences between the 12 media tested. Most cultivars formed the highest percentage of embryogenic callus on the following 4 media: MS2P, MS(x2)2, MS2CHG, and MS(x2)2CHG. Least embryogenic callus was formed on media with 1 mg $l^{-1}$ dicamba and 100 mg $l^{-1}$ cefotaxime. Cultivars responded similarly to MS medium supplemented only with 1 and 2 mg $l^{-1}$ 2,4-D, 2 mg $l^{-1}$ dicamba, as well as to 2 mg $l^{-1}$ 2,4-D media augmented with 5 and 10 mg $l^{-1}$ silver nitrate and 50 mg $l^{-1}$ cefotaxime. Of the four media that gave the highest percentage of callus formation, most cultivars formed calli on media augmented with 100 mg $l^{-1}$ casein hydrolysate, 500 mg $l^{-1}$ glutamine, and with or without twice the concentration of MS inorganic salts. However, casein hydrolysate and glutamine replaced the requirement for twice the concentration of MS inorganic salts, since in the presence of these organic supplements the latter was not necessary. This effect was presumably due to the nitrogen supplement from glutamine. Consequently, MS medium containing 2 mg $l^{-1}$ 2,4-D, 100 mg $l^{-1}$ casein hydrolysate, and 500 mg $l^{-1}$ glutamine was used as the maintenance medium for callus subcultures.

Cefotaxime at the concentration used was without benefit when compared to media containing only 2,4-D. However, more embryos formed calli at the lower concentration of cefotaxime (50 mg $l^{-1}$) than at the higher level. Cefotaxime has previously been used in wheat to significantly improve growth, organogenesis, embryogenesis, and regeneration of immature-embryo-derived calli in culture (Mathias, R. J., L. A. Boyd [1986] *Plant Sci.* 46:217-223).

In recent reports, dicamba has been tested for its effect on cells and embryoid formation in immature wheat embryos (Carman, J. G., N. E. Jefferson, W. F. Campbell [1987] *Plant Cell Tiss. Org. Cult.* 10:101-113; Carman, J. G., N. E. Jefferson, W. F. Campbell [1987] *Plant Cell Tiss. Org. Cult.* 10:115-128). There was no difference between the two auxins with respect to callus formation, whether tested singly or in the presence of kinetin. However, dicamba significantly increased embryoid formation when compared to 2,4-D. In the present study, embryos responded similarly to dicamba and 2,4-D at 2 mg $l^{-1}$, but there was a tendency for immature-embryo-derived embryogenic callus to form embryoids more rapidly on dicamba media than on media with 2,4-D. More embryoids germinated on the lower than on the higher dicamba concentration.

Inflorescences of all cultivars formed embryogenic callus on the 12 media tested. However, irrespective of the cultivars used, embryogenic callus formation occurred at much lower frequencies in inflorescences than in immature embryo explants. Highest percentage of embryogenic callus formation occurred on MS media containing 1 mg $l^{-1}$ 2,4-D as the only growth supplement, followed by media with twice the concentration of inorganic salts, both with and without the organic supplements. Cultivars responded similarly to all other growth media. Of the auxins, 2,4-D promoted more callusing than dicamba at both the concentrations used. The potato extract supplement, which proved beneficial for callus formation from immature embryos, was without benefit for inflorescence culture.

EXAMPLE 3

Cultivars and Growth Condition Response

In 11 of the 12 media, significant differences were observed in the callusing ability of the eight cultivars tested for embryogenic callus formation using immature embryos. 'Chris' formed the highest percentage callusing and 'Coker983' formed the least callus. On medium containing twice the concentration of MS inorganic salts, with casein hydrolysate and glutamine all eight cultivars responded similarly. No significant differences were observed with the inflorescences.

There was little significant difference in embryogenic capacity between field-and greenhouse-grown embryos. Embryos from both growth conditions formed embryogenic calli at high frequencies. Immature embryos of 'Anza,' 'FLA301,' 'FLA302,' and 'Fremont' from the field and greenhouse responded similarly in culture, while 'Hunter' and 'Pavon' immature embryos grown in the greenhouse formed more embryogenic callus than those of the field.

EXAMPLE 4

Explant and Developmental Stage

The developmental stage of the immature embryos was found to be the most important factor for the formation of embryogenic callus. Immature embryos, 1.0-1.5 mm long, showed the best response in culture irrespective of the media, cultivar, or growth condition of the source material. Embryos below or above this optimum size showed lower frequencies of embryogenic callus formation.

EXAMPLE 5

Callus Type and Long-Term Maintenance

Explants cultured on the different callus formation media formed embryogenic as well as the soft, watery, nonembryogenic calli. Within a month of culture two types of embryogenic calli were observed. Immature embryos and inflorescences formed an off-white, compact, nodular, and organized callus. In some instances, few of the explants formed another callus type—a white, compact embryogenic callus. Although somatic embryos were more distinct on the white compact callus than on the off-white type, the white callus was difficult to subculture as it became brown and ceased to grow on maintenance medium.

The immature-embryo- and inflorescence-derived off-white, compact, and nodular embryogenic calli became less organized, less compact, and formed more soft nonembryogenic callus upon transfer to maintenance medium. Therefore, at each subculture, only the more compact and organized pieces were selected and transferred to fresh media. Inflorescence-derived calli after two subcultures became completely brown and necrotic and could not be maintained further. After five successive subcultures (approximately 5 months), the off-white, compact, nodular-organized, immature-embryo-derived embryogenic Type C callus became more prominent. Superficially this callus, referred to as "aged callus," was similar to the previously formed 1-month-old callus. Microscopically, the aged embryogenic callus was also similar to the 1-month-old callus; nodules with distinct epidermis were observed, with small, round, and densely cytoplasmic underlying cells. An off-white, soft, and friable embryogenic callus was obtained after further subculture of the aged compact callus. Microscopically, the friable callus consisted of groups of small, round, densely cytoplasmic cells interspersed with large, elongated, and highly vacuolated nonembryogenic cells. The friable callus grew much faster than the compact callus. At each subculture, the friable callus almost doubled in size and eventually consisted almost entirely of friable callus only. Compact calli grew slower and consisted of more nonembryogenic cells than the friable type.

EXAMPLE 6

Shoot Formation

Immature-embryo-derived embryogenic callus (1 month old) readily formed green shoots on the CC medium. There were no significant differences ($p$ value=0.0588) in the response of calli derived from embryos cultured on the different initiation media. Cultivars formed shoots at high frequencies (up to 100% in most instances) from all the 12 callus initiation media tested, with no significant differences observed between them ($p$ value=0.8612). Initiation media containing silver nitrate or cefotaxime did not show any enhancement of shoot formation, as has been reported with other varieties (Purnhauser, L., P. Medgyesy, M. Czako, P. J. Dix, L. Marton [1987] Plant Cell Rep. 6:1–4; Mathias and Boyd [1986], supra).

The inflorescence-derived calli formed green shoots on all the 12 media tested, and no significant differences were observed between the media ($p$ value=0.0674). Also, the shoot-forming capacity of the cultivars was not significantly different ($p$ value=0.6159). However, when compared with immature-embryo-derived calli, the frequency of shoot formation was lower (50%–60%).

Of the three explant types, callus and shoot formation occurred at lowest frequencies from anthers and anther-derived calli, respectively.

Green shoots obtained from 1-month-old calli derived from immature embryos, inflorescences, and anthers formed roots on the regeneration medium. On transfer to MS hormone-free medium, plantlets increased in size and roots became more extensive. Shoots developed to maturity in the greenhouse.

Green shoots formed from aged immature-embryo-derived calli of all cultivars had poorly developed roots, and transfer to MS hormone-free medium or the different rooting media did not improve root growth. In Vermiculite shoots developed few roots. However, maintaining the plants in a humidity chamber improved growth, allowing transfer of plants to soil and growth to maturity in the greenhouse.

EXAMPLE 7

Production of Transgenic Plants

Table 1 presents results showing the successful production of transgenic wheat plants. These plants were produced by bombarding dishes containing 20–25 pieces (1–3 mm) of 5–7 month old Type C calli with DNA comprising genes for GUS and bar (pBARGUS). Resistant calli were selected by successive culture on 1, 5, 10, 20 and 40 mg/l Basta (20% PPT) at 12–15 day intervals. Selected calli were maintained on 40 mg/l Basta ®.

Alternatively, DNA can be delivered directly into the highly regenerable scutellar cells of immature embryos followed by rapid regeneration and selection of transformants, as was recently demonstrated in rice (Christou, P., T. L. Ford, M. Kofron [1991] Bio/Technology 9:957–962).

TABLE 1

|  | Experiment | | | |
| --- | --- | --- | --- | --- |
|  | PGC1 | PGC4 | PGC6 | PGC8 |
| Cultivar/year | Pavon/90 | Pavon/90 | RH/90 | Pavon/90 |
| No. Calli bombarded with/without DNA | 220/60 | 200/60 | 80/25 | 140/40 |
| No. Calli surviving with/without DNA on 40 mg/l Basta ® | 18/3 | 28/6 | 16/2 | 20/5 |
| No. GUS+ calli/ No. tested | 1/18 | 1/28 | 1/16 | 1/20 |
| No. PAT+ calli/ No. tested | 1/12 | 1/16 | 1/10 | 1/12 |
| Somatic embryos/ shoots/plants | Somatic embryos/ plants | Somatic embryos/ shoots | Somatic embryos/ plants | Somatic embryos/ shoots |
| bar gene present in callus/plants | Callus R0 plants R1 plants | Callus | Callus | Callus |

EXAMPLE 8

Plasmid Delivery and Selection

Five to seven month old Type C embryogenic callus (Redway et al. [1990] Theoret. Appl. Genet., supra; Redway et al. [1990] Plant Cell Rep., supra) of wheat (cultivars Pavon and RH770019) was bombarded with pBARGUS DNA. Calli bombarded without DNA served as controls, and were included in all experiments. The bombarded callus pieces (1–3 mm in diameter) were grown on non-selective MS1 culture medium for 1–2 weeks, and then transferred to MS1B1 medium. Thereafter, the cultures were transferred every two weeks to media with increasing concentrations of the herbicide (5, 10, 20, and 40 mg/l). The surviving calli were maintained on MS1B40 medium. At least 10% of the control calli, as well as the callus pieces bombarded with DNA, failed to grow even on the non-selective medium. No visible growth inhibition or browning of calli was observed on medium with up to 10 mg/l Basta ®, and growth was only partially inhibited (40–50% by visual observation) at 20 mg/l. However, no resistant calli were obtained in two separate experiments where the bombarded calli were transferred directly to MS1B10 or MS1B20 for 2 weeks and then to MS1B40, showing that the step-wise increase in the concentration of Basta ® was important for the selection and continued growth of resistant calli. The results of four separate experiments, in which the bombarded calli were successively grown on media with 1, 5, 10, 20, and finally 40 mg/l Basta ®, are summarized in Table 1.

Figure 2:
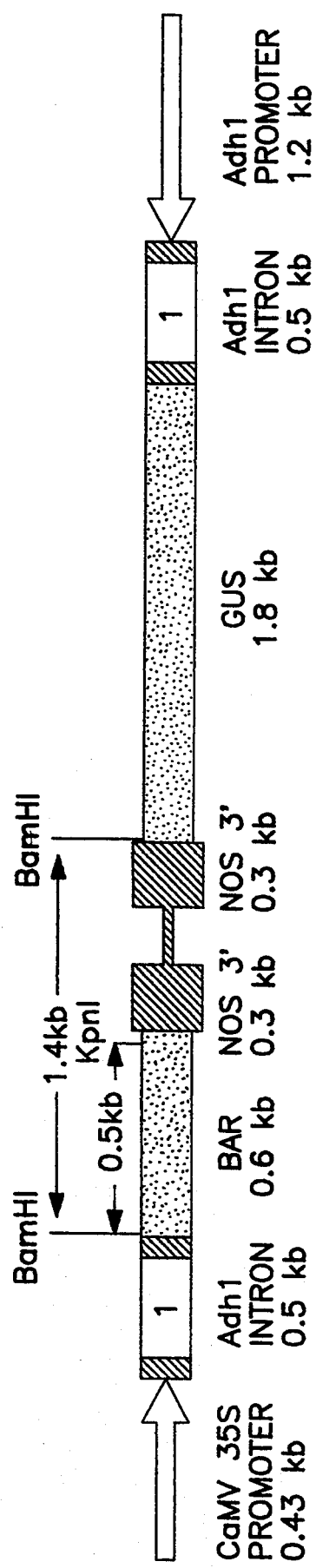
FIG. 2. Schematic representation of pBARGUS plasmid.

Small pieces removed from Basta ®-resistant calli (grown for two subcultures on MS1B40) were tested for GUS activity by X-gluc (Jefferson, supra) histochemical staining. Of the 82 callus lines tested, only three showed blue cells (Table 1). GUS expression was weak and seen only in about 0.5% of cells in the GUS positive callus lines. However, after maintenance on selection medium for 4 months, GUS expression was improved and also seen in a fourth line (Table 1). The weak expression of the GUS gene may be related to its being driven by the Adh1 promoter (FIG. 2).

EXAMPLE 9

Analysis of PAT Activity

Fifty Basta ®-resistant calli (Table 1), as well as some of the control resistant lines, were analyzed for PAT activity by thin layer chromatography. Protein extracts from four independent GUS positive callus lines (PGC1, PGC4, and PGC8 from Pavon, and PGC6 from RH770019) derived from four separate experiments all showed PAT activity. Minor differences were found in the levels of PAT activity between different lines, and a very low level of background activity was also seen in the controls. The four PAT positive callus lines were maintained on MS1B40. During a six months period, they repeatedly tested positive for PAT activity.

EXAMPLE 10

Southern Analysis of Putative Transformed Callus Lines

Genomic DNA isolated from the four PAT positive, as well as the control, calli was digested with BamHI restriction enzyme. Southern blots of the digested DNA were hybridized to a radioactive 0.5 kb bar structural gene fragment from pBARGUS (FIG. 2). Each of the four putative transformed callus lines hybridized to the bar fragment. Additionally, the radioactive probe generated a faint hybridization signal only with the high molecular weight DNA when undigested DNA from one of the callus lines was used, further indicating integration into chromosomal DNA.

EXAMPLE 11

Regeneration of Plants

The four transformed lines were comprised of an organized callus in which well-defined somatic embryos were formed. The callus of the three Pavon lines was very compact, while the RH770019 callus was nodular and easily fragmented. Portions from the four transformed (as well as control) calli were transferred to the regeneration medium containing 5, 10, or 20 mg/l Basta ®, and incubated in light. Within 3 weeks, shoots with green leaves emerged from all four transformed callus lines. No differences were observed in the capacity of the calli to form shoots in the presence of different concentrations of Basta ®. Therefore, 20 mg/l was included in all subsequent regeneration media. No embryos or plants were produced from the control calli.

Shoots produced from PGC1 and PGC6 callus were rooted on medium with 20 mg/l Basta ® (no rooted plants were recovered from the shoots developed from somatic embryos formed in PGC4 and PGC8 calli). The formation as well as the elongation of roots was rather slow in most of the regenerants. Nonetheless, a majority of the plants developed roots over a period of time. Only the rooted plants from PGC1 could be transferred to Magenta boxes containing MS medium with 0.1 mg/l naphthaleneacetic acid, or MS basal medium without any Basta ®. More than 100 rooted green plants were regenerated from transformed PGC1 callus, and at least 75 survived transfer to soil. Forty of these R0 plants were grown to maturity.

A number of the PGC1 plants flowered precociously, some when they were no more than 4–6 inches tall, and had fewer tillers and twisted leaves, all common phenomena in tissue culture regenerants. However, the height of at least 25 of the plants and the size of their inflorescences were nearly comparable to seed derived controls. Although the inflorescences contained normal looking flowers with stigmas and anthers with about 50% filled pollen, in most instances the anthers failed to extrude. In a few plants, the anthers extruded and appeared similar to seed derived plants. However, no seeds were obtained from self pollination. Therefore, wild type pollen from seed derived plants was used to pollinate stigmas of putative transgenic PGC1 plants, and reciprocal crosses were made with pollen from the PGC1 plants to pollinate stigmas of emasculated wild type flowers. Five seeds developed from the pollination of putative transgenic stigmas with wild type pollen, and five from the reciprocal crosses. Due to the slow development of the seeds and in order to ensure the recovery of R1 progeny, immature embryos were removed from the ten seeds and cultured on MS medium 15–20 days after pollination. Two of the embryos obtained from the pollination of putative transgenic stigmas produced normal looking R1 plants which were grown to maturity; the other three embryos did not survive. Each of the five embryos obtained from the pollination of wild type stigmas developed into normal plants. Later, ten more immature embryos were rescued from the pollination of putative transgenic R0 stigmas with wild type pollen. Plants from two of these were transferred to soil.

EXAMPLE 12

PAT and Southern Analyses of Regenerated (R0) Plants

Crude extracts of protein prepared from leaves of each of the 28 randomly selected PGC1 plants showed PAT activity at levels similar to those of PGC1 callus, although approximately a 5-fold increase was seen in two plants.

Genomic DNA isolated from leaves of ten of the regenerants showing PAT activity was analyzed for the presence of the bar gene. Southern blots from the BamHI digested DNA were hybridized to the 0.5 kb bar gene fragment. Each of the ten plants tested showed sequences that hybridized to the bar fragment. The differences between the size of the hybridizing bands of the plant DNA and the bar fragment from pBARGUS digested with BamHI are likely due to the excess amount of DNA which was loaded in order to obtain a strong signal, or to incomplete digestion. No differences were seen between the size of the hybridizing bands of the plant and plasmid DNAs in Southern blots where smaller amounts of the same DNA were loaded, but the signal was rather weak. Undigested DNA included from one of the plants showed hybridization only in the high molecular weight DNA fraction.

The plasmid pBARGUS also contains the non-selectable GUS reporter gene. Therefore, a Southern blot containing uncut and BamHI-digested DNA from PGC1 callus, R0 and R1 control plants was hybridized with a $^{32}$P-labeled 1.8 kb GUS fragment. The uncut DNA from a non-transgenic wheat plant shows no hybridization in the high molecular weight DNA, while the uncut DNA from both R1 transgenic plants do.

A 7.9 kb hybridizing fragment was observed in the lanes containing BamHI-digested DNA from the PGC1 callus, as well as R0 and R1 plants, and was absent in the control non-transgenic plant DNA lane. This band co-migrates with the BamHI-digested pBARGUS standards and is the expected size for the larger BamHI fragment containing the GUS gene (FIG. 2). Larger hybridizing bands of about 11 and 18 kb are also seen in the transgenic DNA lanes. These presumably are due to rearranged copies or border fragments (the pattern is the same since all plants are derived from the PGC1 callus event).

There is also a fainter 5 kb band in all the lanes containing BamHI-digested wheat DNA, including control non-transgenic plant DNA. The intensity of the band correlates with the ethidium bromide staining of the DNA (data not shown) and seems to reflect variation in the amount of the DNA in each lane. Thus, this 5 kb band appears to be non-specific hybridization to repeated wheat sequences. The alternative explanation of minor amounts of contamination seems unlikely since no low molecular weight signals are observed in the uncut lanes of the identical DNA samples. Fortunately, this background band migrates at a different position from the authentic GUS hybridizing bands, as the control plant DNA shows no hybridization at the 7.9, 11, or 18 kb band positions.

EXAMPLE 13

Herbicide Resistance in Transgenic R0 Plants

An aqueous solution of Basta ® (0.001, 0.01, 0.1, and 1.0%) containing 0.1% Tween 20 was applied with a hair brush to the apical one-third portion of the leaves of 12 separate non-transformed plants to assess susceptibility. Each of the leaves treated with 0.001% Basta ® showed necrotic lesions and browning, followed by drying, within 3-4 days. At higher concentrations of Basta ®, the symptoms spread to the entire leaf and even to the tiller. Leaves from 12 transgenic R0 plants painted with 0.001% Basta ® remained healthy and green without any sign of damage, demonstrating the presence of a functional bar gene.

EXAMPLE 14

Analysis of R1 Plants

PAT activity was examined in leaf extracts of four R1 plants obtained from the pollination of transgenic R0 stigmas with wild type pollen, as well as the five plants recovered from the reciprocal crosses. Activity was seen in only two of the R1 plants derived from the first group (one showing a higher level of activity than the other) and in none of the plants from the second group which apparently resulted from self-pollination. The transgenic nature of these two R1 plants was confirmed by Southern hybridization. Additionally, when undigested DNA from one of these plants was used, hybridization was seen to DNA larger than 23.1 kb, indicating integration into chromosomal DNA. The two transgenic R1 plants were further examined for functional activity of the bar gene and showed results similar to those observed with the transgenic R0 plants. The transgenic R1 plant showing a higher level of PAT activity (TR1-6) produced normal flowers which selfed; the second R1 plant (Tr1-7) produced seed from self as well as cross pollination.

EXAMPLE 15

Analysis of R2 Plants

TR1-6 and TR1-7 yielded a total of 262 seeds; 207 from eight spikes of TR1-6 following self-pollination, and 47 from five spikes of TR1-7 after cross-pollination with wild type pollen and 8 from self pollination. 68 seeds were germinated. A total of 57 plants (35 and 22 from three spikes each of selfed TR1-6 and crossed TR1-7, respectively) were used for PAT assays and/or the determination of Basta ® resistance (by application of the herbicide to the second leaf from the main tiller of each 5-week old plant). There was a tight correlation between PAT activity and resistance to the application of Basta ® in all but two of the R2 plants tested. Data presented in Table 2 show the expected 3:1 and 1:1 Mendelian segregation of the bar gene in selfed and crossed progenies, respectively.

TABLE 2

| Progeny of | Sensitivity to Basta ® | | | PAT Activity | | |
|---|---|---|---|---|---|---|
| | No. Tested | No. R | No. S | No. Tested | No. Positive | No. Negative |
| Selfed TR1-6 | 35 | 26 | 9 | 24 | 19 | 5 |
| Crossed TR1-7 | 22 | 11 | 11 | 12 | 6 | 6 |

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for producing transgenic wheat plants, comprising the steps:
   (a) obtaining a Type C embryogenic wheat callus;
   (b) delivering heterologous DNA into the cells of said callus by bombarding said callus with accelerated microprojectiles adsorbed with said DNA;
   (c) selecting for and growing transgenic wheat cells; and
   (d) regenerating transgenic wheat plants from said transgenic wheat cells.

2. The method, according to claim 1, wherein said microprojectiles comprise either tungsten or gold.

\* \* \* \* \*

UNITED STATES PATENT AND TRADEMARK OFFICE
CERTIFICATE OF CORRECTION

PATENT NO. : 5,405,765
DATED : April 11, 1995
INVENTOR(S) : Indra K. Vasil and Vimla Vasil It is certified that error appears in the above-indentified patent and that said Letters Patent is hereby corrected as shown below:

Column 1, line 42: Delete "Dressier" and insert --Dressler--.

Signed and Sealed this

Twenty-fifth Day of July, 1995

Attest:

BRUCE LEHMAN

*Attesting Officer*     *Commissioner of Patents and Trademarks*